(12) United States Patent
Sobel

(10) Patent No.: US 8,600,775 B1
(45) Date of Patent: Dec. 3, 2013

(54) ENHANCED SYSTEM AND METHOD FOR ENHANCING AND SUPPLEMENTING THE INFORMED CONSENT PROCESS OF A PATIENT UNDERGOING A MEDICAL PROCEDURE

(75) Inventor: David Sobel, River Forest, IL (US)

(73) Assignee: EMMI Solutions, LLC, Chicago, IL (US)

( * ) Notice: Subject to any disclaimer, the term of this patent is extended or adjusted under 35 U.S.C. 154(b) by 0 days.

(21) Appl. No.: 13/465,511

(22) Filed: May 7, 2012

Related U.S. Application Data

(63) Continuation of application No. 10/410,749, filed on Apr. 10, 2003, now Pat. No. 8,190,446.

(60) Provisional application No. 60/371,553, filed on Apr. 10, 2002.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ........................................................ 705/2, 3
See application file for complete search history.

(56) References Cited

U.S. PATENT DOCUMENTS

| | | | |
|---|---|---|---|
| 5,557,515 A | 9/1996 | Abbruzzese et al. | |
| 5,799,282 A | 8/1998 | Rakshit et al. | |
| 5,974,446 A | 10/1999 | Sonnenreich et al. | |
| 5,982,509 A | 11/1999 | Ahn | |
| 5,999,909 A | 12/1999 | Rakshit et al. | |
| 6,014,630 A | 1/2000 | Jeacock et al. | |
| 6,171,112 B1 * | 1/2001 | Clark et al. | 434/322 |
| 2003/0216940 A1 | 11/2003 | Sobel | |
| 2008/0306872 A1 * | 12/2008 | Felsher | 705/51 |

OTHER PUBLICATIONS

Office action for U.S. Appl. No. 10/410,749 issued Dec. 28, 2006.
Final Office action for U.S. Appl. No. 10/410,749 issued Jun. 20, 2007.
Office action for U.S. Appl. No. 10/410,749 issued Nov. 16, 2007.
Final Office action for U.S. Appl. No. 10/410,749 issued Jun. 25, 2008.
Office action for U.S. Appl. No. 10/410,749 issued Jun. 9, 2009.
Final Office action for U.S. Appl. No. 10/410,749 issued Mar. 5, 2010.

* cited by examiner

*Primary Examiner* — Robert Morgan
*Assistant Examiner* — Maroun Kanaan
(74) *Attorney, Agent, or Firm* — Marshall, Gerstein & Borun LLP; Randall G. Rueth

(57) ABSTRACT

A method for enhancing and supplementing the informed consent process of a patient undergoing a medical procedure is disclosed. A plurality of interactive multi-media program segments relating to a medical procedure are presented on-line to a patient who is to undergo the procedure. The patient views the multi-media program segments which may include a review of anatomy and physiology, the disease, the procedure, pre and post-operative instructions and risks and benefits. Patients may pose written questions to their doctor. The patient's experience, including which program segments are viewed as well as the patient's interactions therewith are captured, documented and preserved.

18 Claims, 9 Drawing Sheets

ENHANCED SYSTEM AND METHOD FOR ENHANCING AND SUPPLEMENTING THE INFORMED CONSENT PROCESS OF A PATIENT UNDERGOING A MEDICAL PROCEDURE

CROSS REFERENCE TO RELATED APPLICATION

This application is a continuation of U.S. application Ser. No. 10/410,749 filed Apr. 10, 2003, which claims the benefit of U.S. provisional patent application Ser. No. 60/371,553 filed Apr. 10, 2002, the disclosures of which are incorporated herein by reference in their entirety for all purposes.

BACKGROUND OF THE INVENTION

The present invention relates to the process of educating patients and obtaining their informed consent prior to undergoing a medical procedure, and specifically, to an interactive multi-media web based software system that educates the patient as to the medical procedure to be performed, the potential risks and outcomes, confirms the patient's comprehension of the information and documents the exact interactive presentation that the patient has experienced. The present invention supplements the traditional process of obtaining the patient's informed consent and is intended to supplement, though not necessarily replace, the traditional process.

The present system provides a tool that increases patient satisfaction with his/her doctor/surgeon, health care provider and/or hospital, which ultimately serves to reduce the number of patient complaints and most significantly, reduce the amount of litigation brought against doctors and hospitals, and control the dollars awarded in litigation by documenting that patients were indeed aware of the pre-operation and post-operation instructions as well as the risks associated with their procedure. The system described herein is disclosed in the context of patients who are to undergo a surgical procedure, but may be adapted to virtually any health care discipline and enhances the process of obtaining patient informed consent prior to undergoing virtually any medical procedure or prescribed physical or drug therapy.

SUMMARY OF THE INVENTION

A method for enhancing and supplementing the informed consent process of a patient undergoing a medical procedure is disclosed. The method comprises the steps of providing a plurality of interactive multi-media program segments which convey information to a patient regarding the medical procedure to be performed; providing the patient the ability to view the program segments; and providing the patient the ability to interact with the displayed program segments. The invention further comprises the step of capturing the patient's experience, including the program segments viewed and the patient's interactions therewith.

In one embodiment of the present invention, the program segments include a review of the basic anatomy and physiology to which the medical procedure relates, a review of the disease process and how the medical procedure addresses the disease, a review of pre-operative instructions relevant to the medical procedure to be performed, a review of the medical procedure to be performed, a review of post-operative instructions relevant to the medical procedure to be performed, a review of the risks associated with the medical procedure to be performed, a review of the benefits of the medical procedure to be performed, and a review of alternatives to the medical procedure to be performed.

In the preferred embodiment, the present invention further includes the step of providing the patient the opportunity to pose written questions to the doctor or surgeon who is to perform the medical procedure and the step of capturing the patient's experience, includes capturing each keyboard entry, cursor movement and mouse click made by the patient while viewing the presentation.

In one embodiment of the present invention the method for enhancing and supplementing the informed consent process of a patient undergoing a medical procedure comprises providing an online accessible multi-media presentation, displaying each program segment to the patient via an Internet connected personal computer; and documenting each program segment presented to the patient as well as the patient's responses thereto. Accordingly, a permanent record is made memorializing what the patient saw and heard as part of the program segment presentation and each keyboard entry, cursor movement and mouse click made by the patient while viewing the presentation.

A program segment preferably includes text and graphics illustrating the medical procedure to be performed, and a sound recording describing information relevant to the medical procedure to be performed.

In another embodiment, the present invention is embodied in a computer readable media having instructions for presenting a multi-media presentation enhancing and supplementing the informed consent process of a patient undergoing a medical procedure. The instructions performing the steps comprise providing a plurality of program segments directed to the medical procedure the patient is to undergo, displaying each program segment to the patient, an Internet connected personal computer; accepting input from the patient viewing the presentation; and recording each program segment presented to the patient as well as the patient's input responses thereto. It is further preferred that the recording made of the program segments and the patient's responses thereto is stored on second computer readable storage media.

BRIEF DESCRIPTION OF THE DRAWINGS

For a better understanding of the method for enhancing and supplementing the informed consent process of a patient undergoing a medical procedure, reference may be had to preferred embodiments shown in the following drawings in which.

DETAILED DESCRIPTION

Figure 1:
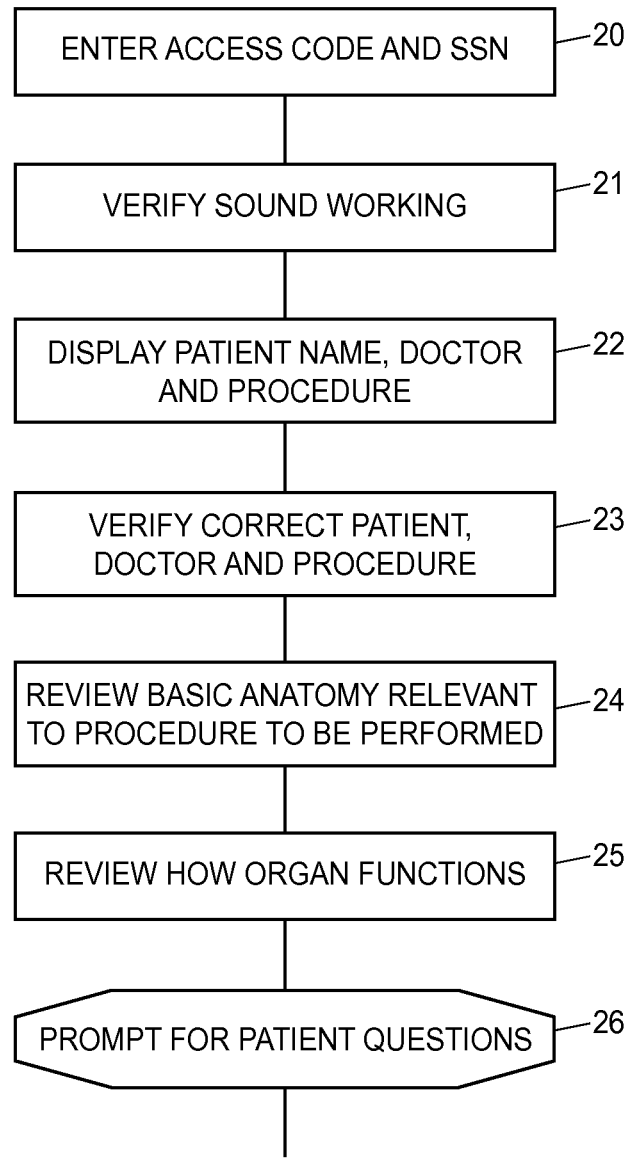
FIGS. 1-3 illustrate a flow diagram of the steps of the inventive method disclosed herein.

A better understanding of the objects, advantages, features, properties and relationships of the method for enhancing and supplementing the informed consent process of a patient undergoing a medical procedure will be obtained from the following detailed description and accompanying drawings which set forth illustrative embodiments which are indicative of the various ways in which the principles of the invention may be employed. Referring now to the figures, wherein like reference numerals refer to like elements, the present method for enhancing and supplementing the informed consent process of a patient undergoing a medical procedure is described.

The present system provides the patient with a series of short interactive multi-media programs directed specifically to the medical procedure the patient is to undergo and which serves to enhance and support doctors and health care professionals in the process of delivering informed consent. As described below, each program experience provides patients with a working understanding of their upcoming medical procedure; its risks, benefits, and aftercare. The program content distills difficult and often confusing information into simple everyday language and clear animations.

In a preferred embodiment of the present invention it is contemplated that the system be administered entirely over the Internet where the library of content resides solely on central server(s) and patients access and may download content from the server(s) via a secure web site. In an alternative embodiment, the patient may be provided with a CD-ROM and instructions on how to access the system's computer network that serves to capture the patient's experience. The CD-ROM contains the media rich interactive content that the patient will experience. It is contemplated that the system will utilize CD-ROMs in situations where Internet bandwidth limitations exist that prevent full use of a media rich— memory heavy application.

Figure 2:
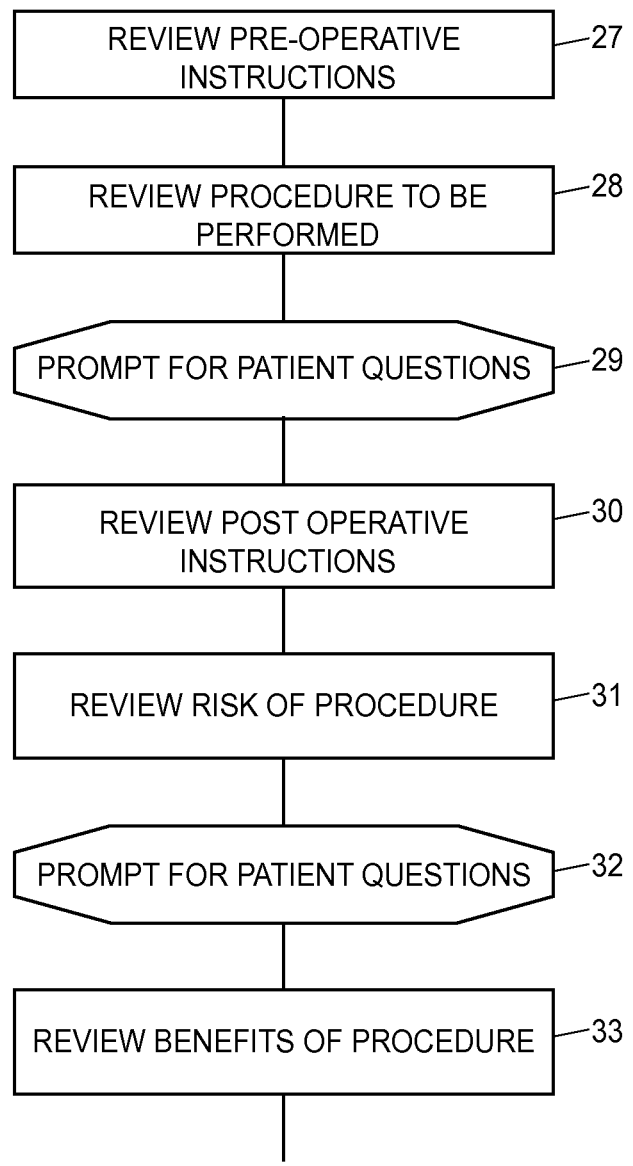
Figure 3:
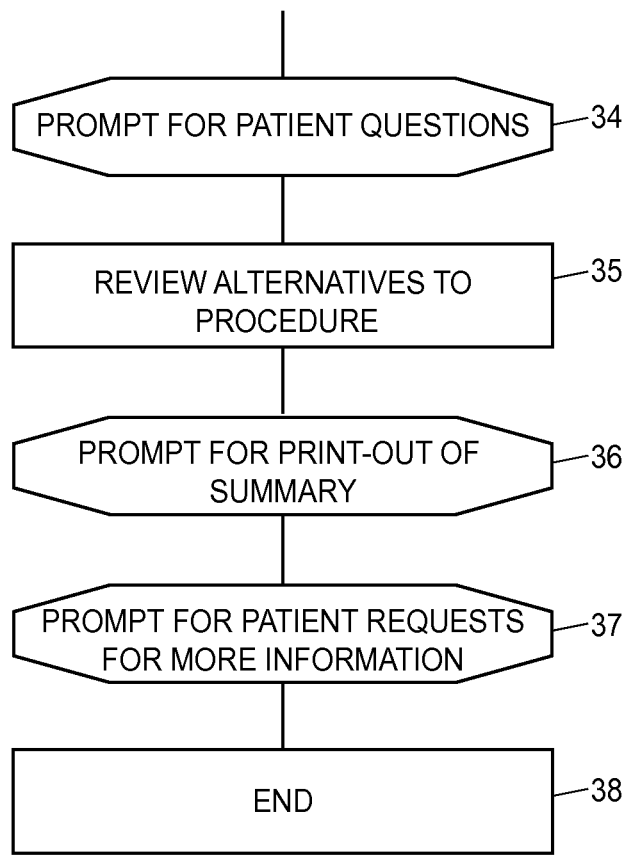

For convenience the method according to the present invention as illustrated in FIGS. 1-3 will be described below with reference being made, as appropriate, to the various steps which comprise the present method.

System Administration—

The doctor or hospital who will be performing the surgery initially registers the patient with the system administration server and is in turn provided with an access code. The surgeon or an assistant uses the system administration website to enter or identify (via a secure connection) the patient's name, the doctor's name, the procedure to be performed and the hospital. Additionally, other patient identification information may be provided, such as a social security number. The present system can be implemented in a single hospital by a single doctor or multiple doctors, or across a wide geographical region composed of many hospitals and doctors.

The Patient Experience—

In the preferred embodiment of the invention, the patient interacts with the system solely via the Internet by accessing a web page.

Figure 7:
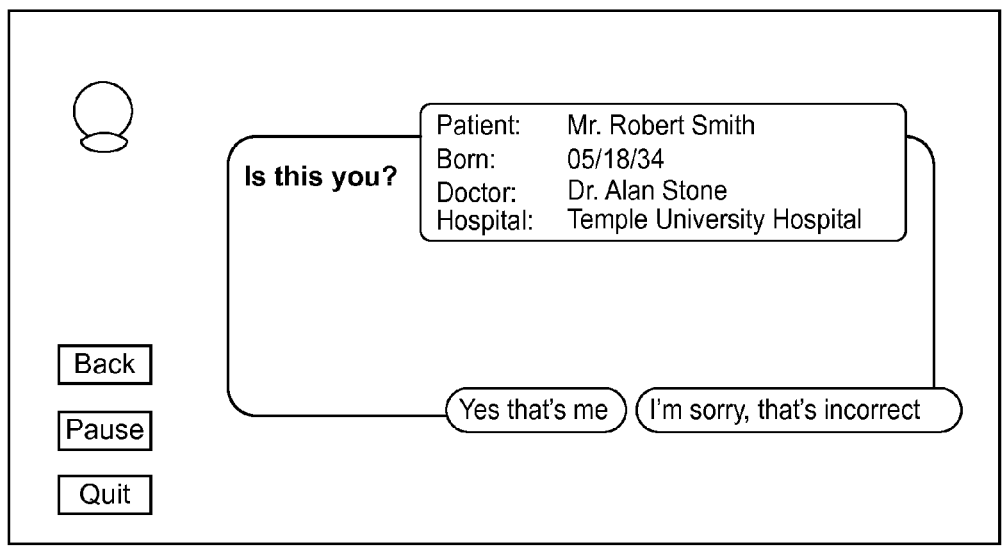
FIG. 7 illustrates a display used to verify the correct patient and procedure.

During an office visit the doctor or surgeon provides the patient with an access code and instructions how to access the system website. In the preferred Internet/web based system, using any Internet connected computer, the patient accesses a specified URL and is prompted to enter their password/access code, step 20. Preferably, the patient is presented with a short audio introduction and is prompted to confirm that they indeed can hear the sound, step 21. In the event that the patient responds negatively, the system may choose to abort the presentation inasmuch as the patient may not receive the full benefit if the audio component is missing. The patient is next greeted with a personalized message stating their name, their doctor, the procedure they are to have and where they are having it performed, step 22, and the patient is prompted to confirm that the information displayed is correct, step 23. A sample display screen is illustrated in FIG. 7. The access code identifies the patient and dictates which program the patient is presented with via the Internet, or from the CD-ROM.

The patient may also be provided the opportunity to use the present system in a hospital or doctor provided education center which has computers with Internet access, or the patient may take a CD-ROM to their own home to run on their own PC, as long as they have the ability to access the system administration server web site through a suitable connection, such as a dial-up modem.

The access code provided by the doctor or surgeon preferably expires at midnight before the scheduled surgery. As described below, expiration precludes the patient from using the system at the last minute and prevents the patient from composing questions for the surgeon which may not reach the surgeon before the scheduled procedure. Alternatively, the present system may be configured to permit the patient to use the system at any time prior to surgery and in this way gain comfort and relieve anxiety the night prior to surgery, but with a question mode being disabled at a pre-determined time prior to the scheduled surgery.

The present system supplements the doctor's verbal description of the medical procedure and risks and pre and post-operative events. The patient watches and participates in an interactive audio-visual presentation during which information is presented. The presentation preferably includes sections regarding physiology, pathophysiology, an explanation of the procedure to be performed, risks and benefits to the procedure, alternatives to the procedure, pre-operative instructions, postoperative course and post-operative recommendations. The presentation may be interactive wherein patient responses are solicited during the course of viewing each of the sections. The system may accordingly require the patient to provide an affirmative input to acknowledge that the patient has understood the section or has no questions before being able to proceed to the next section. It is preferable that any content dealing with the risks and benefit of a medical procedure require patient confirmation.

Topics and subjects addressed in the presentation include, but need not necessarily be limited to the following.

Review of the Basic Anatomy and Physiology—

Figure 8:
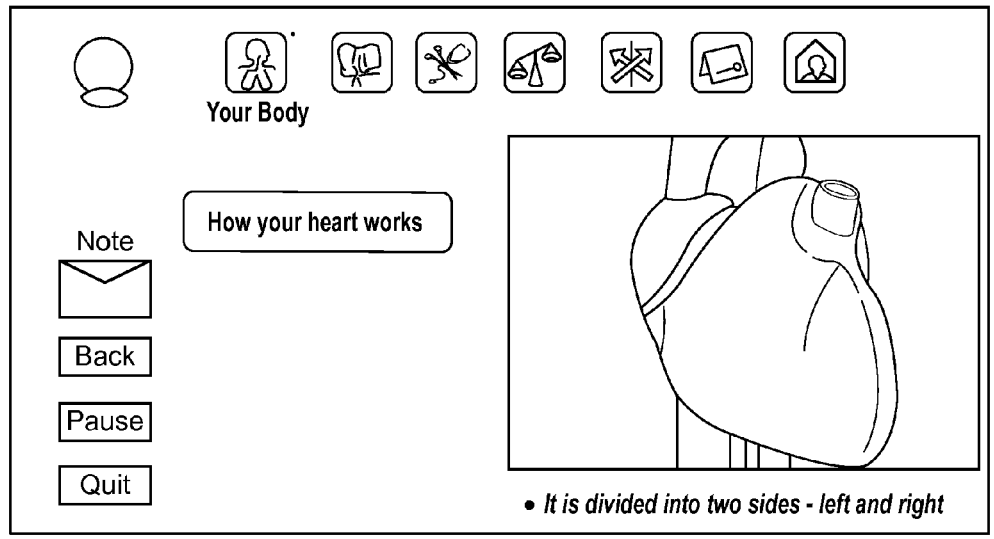
FIG. 8 illustrates a display of a program element reviewing the anatomy of an organ relevant to the medical procedure.

The program content presented to the patient may begin with a presentation which reviews the basic anatomy relevant to the medical procedure the patient is to undergo, step 24. For example, a patient undergoing eye surgery may be presented with a brief tutorial explaining how the human eye works, while a patient undergoing a coronary by-pass may be presented with an explanation how the human heart functions when working properly, FIG. 8.

Figure 4:
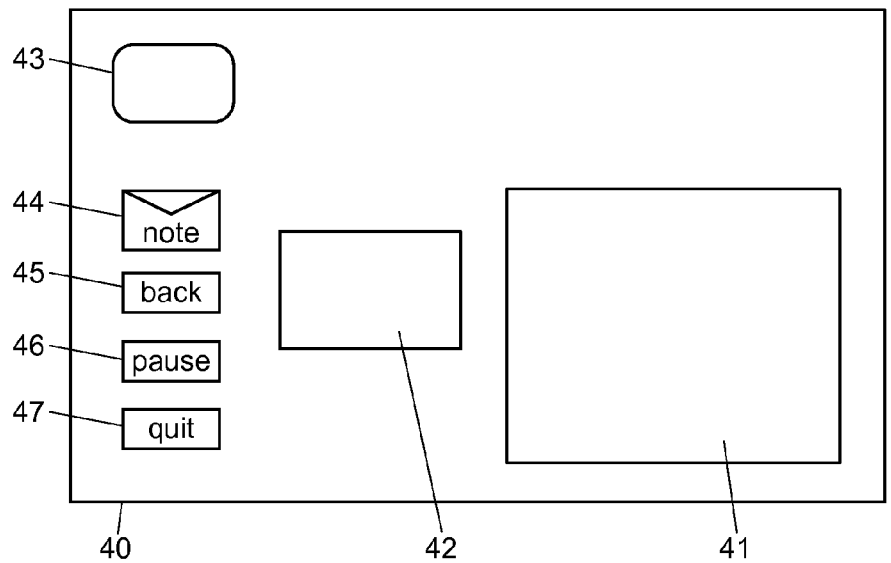
FIG. 4 illustrates a form of generic display presented to a patient using the present inventive system and method.
Figure 5:
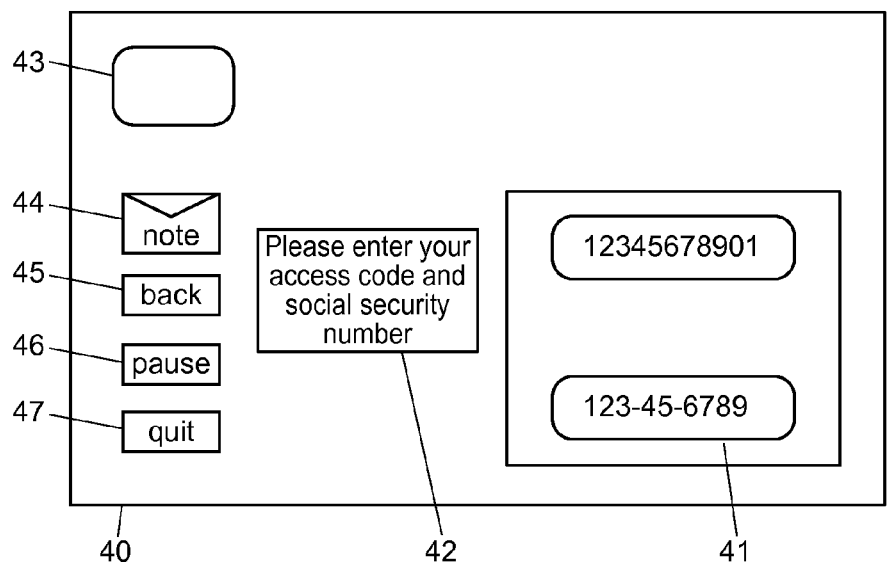
FIG. 5 illustrates an access code entry screen.
Figure 6:
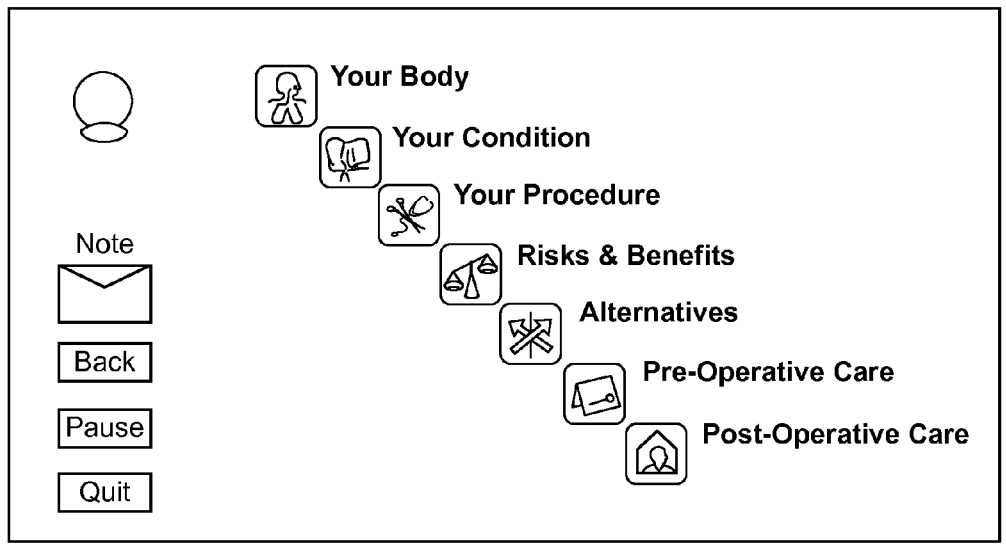
FIG. 6 illustrates a general display highlighting the various program elements to be presented to the patient using the present inventive system and method.

The basic screen display presented to the patient is illustrated in FIG. 4. Within overall display 40 appears various visual components. The graphic information presented to the patient is depicted as appearing in region 41 which may also be accompanied by textual display appearing in region 42. To permit the patient to control the presentation various control buttons are provided which may be accessed using a convention PC mouse or cursor control device, or keyboard command. Button 44 serves to permit the patient to enter the notes mode and compose a written question which the system will transmit to the patient's doctor or surgeon. Button 45 permits the patient to backup the presentation to the immediately prior program segment. Button 46 permits the patient to pause the presentation and button 47 permits the patient to exit. Logo 43 is provided to permit the administrator, doctor or hospital to personalize the presentation. FIG. 6 illustrates the various program segments which the patient is expected to view.

The Need for the Procedure—

The preferred embodiment of the present system preferably next addresses the subject of how the procedure relates to the relevant organ—in short, why the patient needs the procedure, step 25. During this portion of the presentation, the patient may view a description of the disease the patient has and/or the reason for surgery. The system may further provide relevant normal physiology and anatomy as well as the pathophysiology. As in each program segment, the presentation preferably includes both audio and visual components. The audio component may include a voice-over preferably spoken by a "friendly" but authoritative voice selected to diminish patient anxiety. The visual components may include still or motion picture images. In the preferred embodiment, the images are not photo-realistic but are presented instead in a "softer" less threatening style.

Prompts for Questions—

At this point, the system prompts the patient to pose questions for his or her doctor, step 26. As described below, the present system provides the patient with the ability to compose a question by typing it directly into the PC upon which the presentation appears.

Review of Pre-Operative Instructions—

The system next presents the patient with information relevant to preoperative planning, cautions and instructions, step 27. The patient may be cautioned and advised to inform their doctor of all medications or other supplements they may be taking. The patient may be warned to stop certain activity at a predetermined period prior to the procedure. The presentation may also give the patient information relevant to the day of surgery, such as where to register within the hospital, insurance related information and other details which the surgeon may wish to remind the patient of prior to the procedure, such as to fast the day before surgery or discontinue certain medications.

The Procedure Itself—

Figure 9:
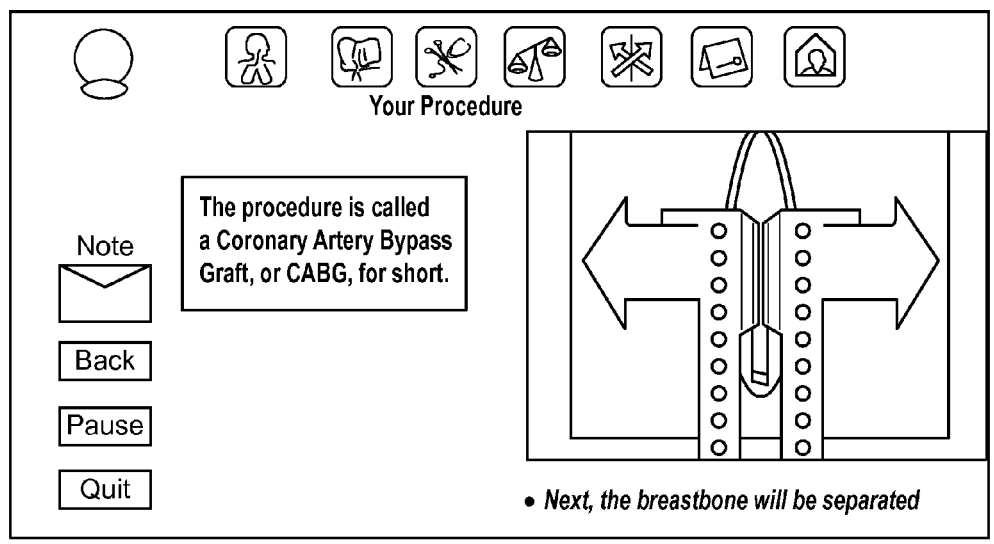
FIGS. 9-11 illustrate displays of the program element which review the medical procedure to be performed.
Figure 10:
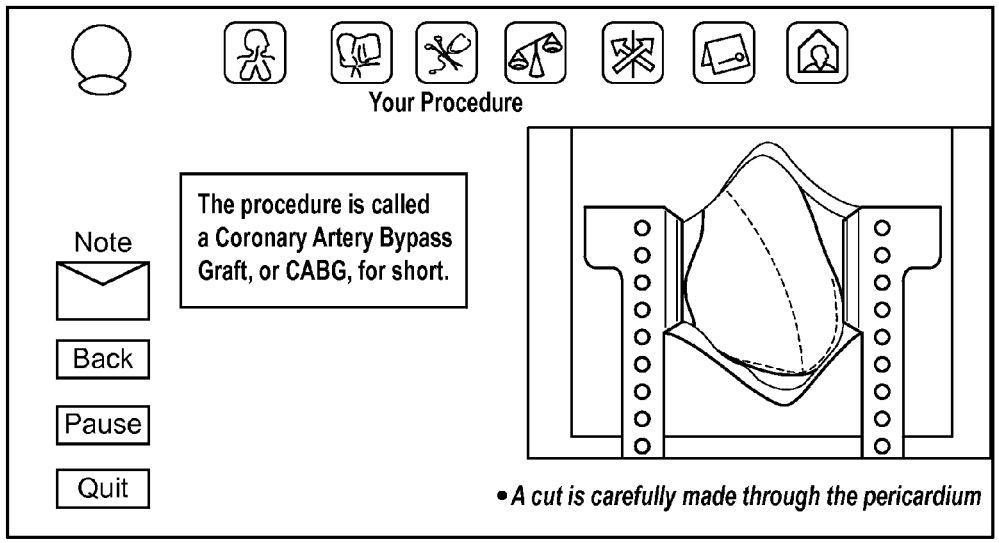
Figure 11:
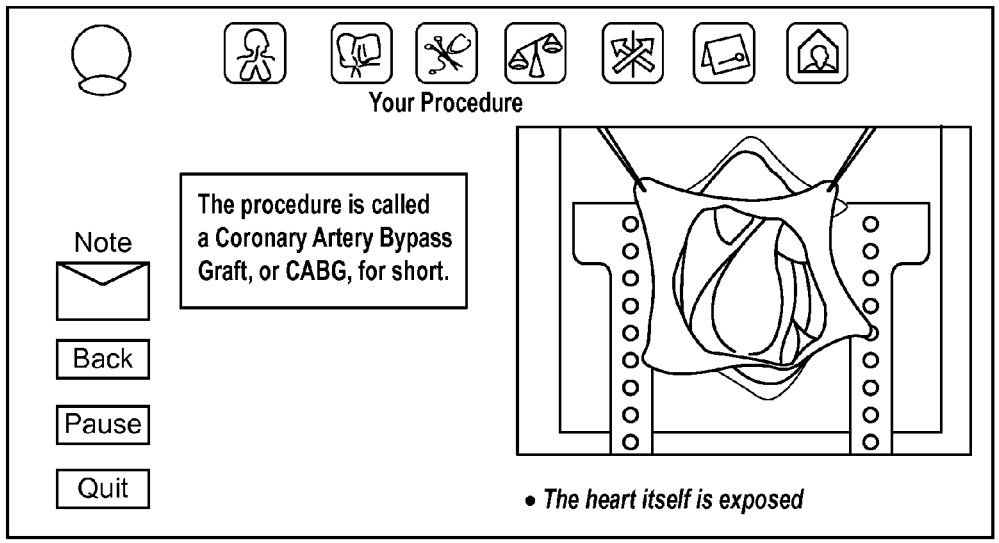

The next subject presented to the user addresses the medical procedure to be performed, step 28. Again using audio and visual content the medical procedure is described. The discrete steps which the surgeon may perform may be addressed generally or in detail. The procedure may be presented using a single or a series of images or alternatively a motion picture or animated presentation. FIGS. 9-11 illustrate an explanation which may be given to a patient scheduled to undergo a coronary artery bypass. The program segment may discuss the time required to perform the procedure and the instruments and sedatives to be used. Following this program segment the patient may again be prompted to pose questions to their doctor or surgeon, step 29.

Post Operative Information & Care Instructions—

Again using audio and visual images the patient is next presented with content that informs the patient as to the optimal post-operative care, step 30. For example, the patient may be instructed to remain in bed or to avoid solid food for a given period of time. Pain medication can also be discussed and instructions revised. The patient may be presented with information relative to the recovery process, side effects, post-operative medications and warning signs which should trigger a call to the doctor or surgeon. The patient may also be presented with the option of having instructions printed or downloaded to the patient computer for later reference.

Risk Factors & Benefits—

The risk factors and benefits are next presented to the user, step 31. Using voice and graphics the patient is presented with the various risks associated with the medical procedure in a non-threatening manner. At each stage the patient may be presented with the option to learn more information about the risk just discussed, step 32. In this manner the patient may learn more details and as described below, may compose questions to their doctor pertaining to the risk or risks. In one embodiment, the user may be given the option to merely flag a given risk, thereby indicating to the doctor that the patient wishes to further explore and discuss that particular risk factor associated with the procedure without having to compose a detailed question. The benefits associated with and offered by the procedure are likewise addressed, step 33. Following this program segment the patient may again be prompted to pose questions to their doctor or surgeon, step 34.

Alternatives—

Lastly, the patient may be presented with content that discusses alternatives available to the patient in lieu of the relevant medical procedure, step 35. The patient may be presented with information relative to alternative surgical procedures, procedures which are in development but not yet available as well as non-surgical alternatives.

Printed Summary—

The system preferably prompts the patient to respond whether they would like to obtain a printed summary of the information presented in the various program segments, step 36. If elected, the system will generate a hard copy printout on the patient's local PC printer.

Additional Information—

Lastly, the patient is prompted to respond whether they would like to receive additional information relative to the procedure, new developments and procedures and new medications, step 37. After this step, the program ends, step 38.

As discussed, at each stage, the system presents the patient with a multi-media presentation comprising both audio voice over, music, on-screen text, and animation, as well as still illustrations. The substantive content is presented to the patient in a friendly fashion, specifically designed to be easy to understand. In a preferred embodiment, the substantive content is written on a sixth grade level so that it will be accessible to the masses. The system is designed to provide the patient with a mastery of knowledge appropriate for the patient and to provide information in a manner which maximizes the cognitive absorption by the patient. Moreover, the illustrations are designed to be informative and educational but not so detailed in nature as to arouse additional patient anxiety.

Furthermore, in order to proceed from one subject to the next the patient must take affirmative action, such as by clicking on a designated area on the screen using the computer mouse or by striking a certain key on the computer keyboard.

Doctor Question Feature—

One feature of the present system is the ability for patients to have the opportunity to pose questions to their doctor. The program provides the patient the option of asking questions to the doctor during the course of viewing the multi-media presentation. Alternatively and/or in addition, the program can also permit the patient to ask questions at the end of the program. In each case, the patient asks questions by simply typing a question into a screen generated by the program. The question or message is treated much like an email and is forwarded by the system to the doctor or surgeon. When the patient completes the program, the doctor/surgeon is altered by the system notifying them that the patient has completed the process and that the patient posed the following questions.

The doctor may respond in writing by composing a reply message which the doctor sends to the system. To maintain patient privacy, the system may simply send an anonymous email to the patient Internet email address alerting them that they have one or more unread emails on the system server, or may simply email directly to the patients pre-existing email account if the patient so chooses.

In order to not burden a doctor or surgeon, the present system may instead, allow the patient to ask questions, but inform them that the doctor will not reply in an email. Rather, it is left to the doctor to print out the list of questions and concerns that each patient has and can meet with the patient to discuss those questions. At that time, the doctor may have the patient sign a statement at the bottom of the list of questions attesting to the fact that they had the opportunity to discuss the questions with their doctor.

The system can thus also serve as a communication hub to provide a channel and facilitate communication between a patient and health care provider. The names and email addresses of each hospital and doctor treating a patient can be available to the patient. The system server can similarly track and archive the messages passed between patient and doctor to preserve the record. The communication hub may also permit the hospital to later send messages to the patient altering them to new health care issues or "medical specials", promoting, for example, stroke awareness month. Again to preserve privacy, the patient can elect to use code names.

Data Capture Feature—

One significant aspect of the present invention is the data capture function which is executed in a manner transparent to the patient. The system administration server performs the data capture function. Throughout the entire presentation, the system server documents and catalogs the exact experience that the patient is undergoing. The system server tracks when the patient first accessed the Internet website (or accessed a CD-ROM given the patient), how many individual viewing sessions took place, exactly what content was viewed and for how long. In one embodiment, the present system tracks and logs every patient "mouse click" and time stamps each event. If questions are posed by the system to the patient, the system captures the answer to every question the patient was asked, to serve as confirmation of mastery of knowledge. The server can also solicit patient feedback and track and log patient responses.

Since the system administration server has captured and cataloged the exact experience that the patient has undergone in its database, the patient's exact experience can be recreated if need be at a future date. Moreover, a doctor or hospital is provided with the ability to access the system server prior to surgery to verify that the patient indeed viewed the presentation. The doctor may be given an indication that the patient did not understand certain sections or gave an express indication that more information was needed. The doctor can then address those issues face-to-face with the patient prior to surgery. The hospital may decide that no surgery will be performed unless and until the patient views the presentation.

While the patient controls the pace at which the presentation advances, the system may display prompts to the patient asking that they confirm whether or not they are comfortable proceeding with the program. Periodically offering the patient the option of posing a question to their doctor requires a response absent which the program does not continue. This provides an opportunity to assure that information is being conveyed in an understandable fashion to the patient and moreover assures that the patient does not have the ability to race through the program since the option to proceed to the next section will not be presented until all of the information for a particular topic or stage has been presented.

An additional feature of the present invention relates to the patient having the opportunity to elect to receive further information regarding their disease or surgery or new treatments that may become available. The patient may provide a street or an email address in a HIPAA compliant manner. The patient's acquiescence to receiving further information can be captured, which data can be leveraged at a future date with respect to marketing opportunities. For example, a patient undergoing a heart by-pass procedure may indicate a desire to receive information pertaining to new medications offered to treat a relevant condition. The system provider can convey this information to a drug company in exchange for a fee.

The present system can be customized for insurance companies, as well as hospitals and certain physician groups, whereby the patient viewed screens that can be personalized to each of these entities allowing the entities to infuse their logos and personalized look to certain aspects of the experience.

In another embodiment, the system may provide auxiliary access codes to be used by other family members whereby the system can track that a patient's spouse or parent likewise viewed the presentation and understood the content provided relative to the medical procedure to be performed. In the event a patient or family member later makes a claim or files a lawsuit, the data captured by the system can be used to confirm exactly what information was not only provided to the patient, but exactly what information the patient actually viewed. The exact multimedia experience tailored to the patient's actual medical procedure having been documented by the system can be recreated and played for a judge or jury. The present system thus provides a risk management tool that may be used by doctors, hospitals and insurance companies to supplement the process of informed consent.

Patients who receive the disclosure provided by the present system are more likely to do well, to recover quicker by having a better mental outlook and better satisfaction with the doctor and hospital. Patients who experience post-operative infections and/or pain, who miss work due to extended recovery periods or experience, will have been advised of these possibilities and more importantly will have been educated such that they are less likely to blame the doctor or hospital. Fewer unexpected outcomes will lead to fewer claims and lawsuits.

Other Uses—

The present system may also be used in non-surgical procedures, such as physical or drug therapy, and end of life issues. For example, a patient may be provided with a presentation detailing the nature of the physical therapy recommended by a doctor or the nature of the medication the doctor has prescribed. The effect of the drug, possible side effects, warning signs, drug interaction and other information can be provided to the patient.

Hardware Components—

Figure 12:
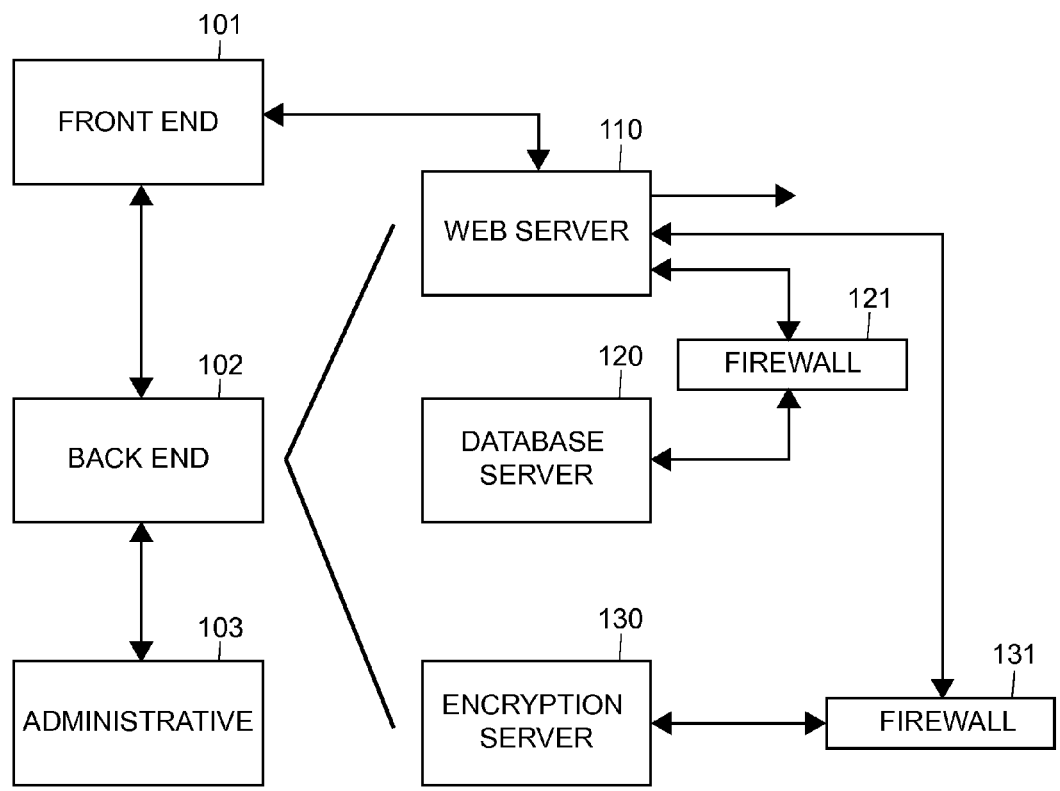
FIGS. 12-13 illustrate a schematic diagram of the structure of basic hardware components which comprise the present system.

FIG. 12 of the drawings illustrates the three main components which comprise the present system, namely front end 101, which presents content to the patient; back end 102, which delivers content to the front end and captures the patient experience; and administrative component 103, which allows the medical practitioner to enter patient information, monitor patient progress, and receive patient questions on the procedure.

As described above, the process starts at the medical practice with an administrator entering patient information into the system which causes the system to generate an access code for the patient. This access code is preferably a random string of numbers. The number contains no information in and of itself, but can be tied back to the patient's personal data, scheduled procedure, and the medical practice that issued it.

The patient uses the access code together with a second form of identification such as social security number, to log into the present system. The front end 101 sends the access code to the back end 102, which verifies the access code and returns the procedure information, as well as the educational content. As the patient moves through the program, his click stream is recorded by the back end 102.

In some situations it is vitally important to make sure that the patient's actions have been captured. Since the present system is implemented over the Internet, which is at times an inherently unreliable network, one can never be absolutely certain that a message sent from one point has reached another. To guard against information loss of this type a hand-shake mechanism can be implemented where for example at times the front end, after sending click stream data to the back end, will wait for a response before proceeding further. The back end 102, in turn, will not send a further response to the front end until after the click stream has been recorded. If the front end 101 does not receive a response within a certain amount of time it will repeat the previous message. This ensures that there is no data loss, even at the expense of capturing multiple copies of the same click stream message in the system logs.

One such situation is when a patient asks a question. The ability to deliver thoughtful questions to the doctor is a major component of the present system, and so it is critical that such questions not be lost. At any point in the program a patient can pose a question by clicking on the letter icon. Once written, send or continue is pressed and the patient is brought back into the informational portion. Behind the scenes, the front end now sends the question to the back end 102, and will wait for a response before proceeding. As a double check method, the questions are also sent all together at the end of the program.

Figure 13:
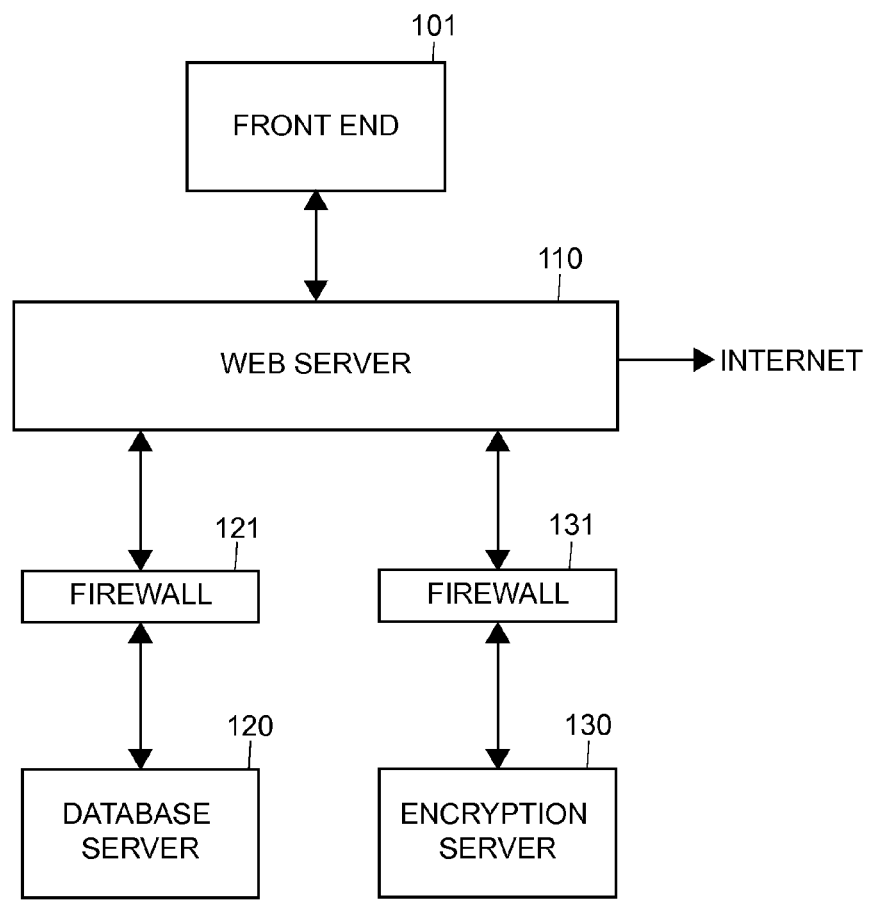

The system back end 102 is preferably separated into three functional units, illustrated in FIGS. 12 and 13 as including web server 110, database server 120, and encryption key server 130. The web server 110 handles the delivery of content to the front end 101, and records the user's click stream. It also acts as an interface so that the database does not have to reside directly on the Internet. The database server 120 sits behind a firewall 121, and will only accept connections from the web server 120. All patient data is stored on the database server 120. Finally, the encryption key server sits on a separate computer 130, also behind a firewall 131. The key server accepts connections only from the web server 110 and hands out the encryption key needed to encrypt or decrypt the patient name. By always keeping the patient name encrypted on disk and the encryption key separate from this disk, the present system serves to maintain patient data anonymously so that even in the event of physical theft of the database patient privacy is ensured.

The administrative component 103 sits on the web server 110 and acts as an interface for the medical practice. Practice administrators can enter patient and surgery information, follow patient progress, and access patient questions for the doctors. After entering a patient's name, it is encrypted before being stored in the database 120. When retrieved, the name is decrypted and displayed on the screen, but not stored anywhere on the web server itself.

Security—

All communication which travels over the Internet is encrypted. This protects against the unlikely event that someone is eavesdropping on communications with the backend or administrative component. While eavesdropping can still occur, the data collected would be indecipherable and indistinguishable from random characters. Standard data security methods are also employed, such as firewalls and intrusion detection, to ensure the integrity of the entire system.

CD-ROM Version—

In the CD-ROM based embodiment of the present invention the process begins with the patient loading a CD-ROM into a computer. The CD-ROM is provided to the patient to take home and use on the patient's home computer. The CD-ROM containing the multi-media content and other software programming which form part of the present system can be run on a conventional PC having the ability to connect to a central administration computer server either by direct dial or via the Internet. The central administration server controls the overall system operation, including security and data capture, as described below.

The system automatically launches a software program which establishes a connection to the system administration server. The patient is prompted to provide their access code toward identifying the patient. The administration server may optionally obtain search information and may solicit further identifying security information to confirm that this is indeed the patient who will be undergoing the procedure. The user code thereafter prompts the CD-ROM as to which portions of the media are to be presented to the patient. The patient then views the multi-media experience. The patient controls the pace at which the information is presented and is able to return to any information that they feel is necessary to review.

While specific embodiments of the invention have been described in detail, it will be appreciated by those skilled in the art that various modifications and alternatives to those details could be developed in light of the overall teachings of the disclosure. Accordingly, the particular arrangement disclosed is meant to be illustrative only and not limiting as to the scope of the invention which is to be given the full breadth of the appended claims and any equivalents thereof.

What is claimed is:

1. A computer-implemented method for informing a patient via an Internet-connected computing device, the patient experiencing a medical issue, the method comprising:

receiving, via the Internet, an access code from a patient front end computing device at a back end server, the access code corresponding to a patient identification for a patient experiencing the medical issue;

causing a processor to determine a plurality of multi-media segments based on the received access code;

causing a processor to send, via the Internet, the determined plurality of interactive multi-media segments to the patient front end computing device in response to receiving the access code, the plurality of interactive multi-media segments conveying information to the patient regarding the medical issue;

receiving, via the Internet, patient experience data at the back end server, the patient experience data corresponding to the access code patient identification and one or more of the segments sent, the patient experience data including an indication of patient interaction with one or more of the sent segments;

causing a processor to encrypt the patient identification;

causing a processor to record the patient experience data with the encrypted patient identification at the back end server;

receiving, via the Internet, a request from a medical practice front end computing device at the back end server for at least a portion of the patient experience data, the request including the patient identification;

causing a processor to encrypt the patient identification from the request;

causing a processor to determine match the encrypted patient identification from the request to the encrypted patient identification that is stored with portion of the patient experience data to satisfy the request;

causing a processor to send, via the Internet, the determined matched portion of the patient experience data to the medical practice front end computing device in response to the request from the medical practice front end computing device;

wherein the request allows the medical practice to monitor the progress of the patient viewing the interactive multi-media segments.

2. The method of claim 1, further comprising encrypting data sent or received via the Internet, the data including one or more of the access code, the patient identification, the plurality of interactive multi-media segments, and the patient experience data.

3. The method of claim 1, wherein the patient identification includes a patient name.

4. The method of claim 1, further comprising storing the patient experience data at the back end server upon receiving the patient experience data from the patient front end computing device.

5. The method of claim 4, further comprising encrypting the patient identification before storing the patient experience data at the back end server.

6. The method of claim 1, wherein the patient experience data corresponds to a first segment of the plurality of interactive multi-media segments sent to the front end computing device.

7. The method of claim 6, wherein sending the plurality of multi-media segments to the front end computing device includes sending a second segment only after receiving patient experience data corresponding to the first segment.

8. The method of claim 7, wherein the patient experience data includes one or more of a keyboard entry, a cursor movement and a mouse click made by the patient while viewing the plurality of interactive multi-media segments sent to the patient front end computing device.

9. The method of claim 1, wherein the access code includes one or more of a code provided to the patient or a family member of the patient.

10. The method of claim 1, wherein the back end server includes a web server that stores the plurality of interactive multi-media segments and the patient experience data, and sends the multi-media segments to the patient front end computing device and the patient experience data to the medical practice front end computing device through a firewall.

11. The method of claim 1, further comprising sending, via the Internet, a prompt to the patient front end computing device to enter the access code.

12. A computer system for informing a patient via an Internet-connected computing device, the patient experiencing a medical issue, the system comprising:

a web server including a processor and a memory, the memory including an Internet-accessible multi-media presentation including a plurality of multi-media segments directed to a medical issue the patient is experiencing and instructions for execution on the processor to:

receive, via the Internet, an access code from a patient front end computing device, wherein the access code corresponds to a patient identification for the patient experiencing the medical issue;

cause a processor to determine a plurality of multi-media segments based on the received access code;

cause a processor to send, via the Internet, the determined plurality of interactive multi-media segments to the patient front end computing device in response to receiving the access code, wherein the plurality of interactive multi-media segments convey information to the patient regarding the medical issue;

receive, via the Internet, patient experience data corresponding to the access code patient identification and one or more of the segments sent, wherein the patient experience data includes an indication of patient interaction with one or more of the sent segments;

cause a processor to encrypt the patient identification;

cause a processor to record the patient experience data with the encrypted patient identification at the back end server;

receive, via the Internet, a request from a medical practice front end computing device at the back end server for at least a portion of the patient experience data, the request including the patient identification;

cause a processor to encrypt the patient identification from the request;

cause a processor to determine match the encrypted patient identification from the request to the encrypted patient identification that is stored with portion of the patient experience data to satisfy the request;

cause a processor to send, via the Internet, the determined matched portion of the patient experience data to the medical practice front end computing device in response to the request from the medical practice front end computing device;

wherein the request allows the medical practice to monitor the progress of the patient viewing the interactive multi-media segments.

13. The computer system of claim 12, further comprising an encryption apparatus including instructions for execution on a processor to encrypt data sent or received via the Internet, the data including one or more of the access code, the patient identification, the portion of the plurality of interactive multi-media segments, and the patient experience data.

14. The computer system of claim 12, wherein the web server further includes instructions for execution on the processor to store the patient experience data corresponding to the patient identification upon receiving the patient experience data.

15. The computer system of claim 14, wherein the encryption key server further includes instructions to encrypt the patient identification corresponding to the patient experience data before the web server instructions store the patient experience data corresponding to the patient name.

16. The computer system of claim 12, wherein the patient experience data corresponds to a first segment of the portion of the plurality of interactive multi-media segments sent to the patient front end computing device.

17. The method of claim 16, wherein the web server instructions to send the portion of the plurality of multi-media segments to the patient front end computing device includes an instruction to send a second segment only after executing an instruction to receive patient experience data corresponding to the first segment, wherein the patient experience data includes one or more of a keyboard entry, a cursor movement and a mouse click made by the patient while viewing the plurality of interactive multi-media segments sent to the patient front end computing device.

18. A non-transitory computer-readable storage medium including non-transitory computer-readable instructions stored thereon for informing a patient via an Internet-connected computing device, the patient experiencing a medical issue, the instructions to:

receive, via the Internet, an access code from a patient front end computing device, wherein the access code corresponds to a patient identification for the patient experiencing the medical issue;

cause a processor to determine a plurality of multi-media segments based on the received access code;

cause a processor to send, via the Internet, the determined plurality of interactive multi-media segments to the patient front end computing device in response to receiving the access code, wherein the plurality of interactive multi-media segments convey information to the patient regarding the medical issue;

receive, via the Internet, patient experience data corresponding to the access code patient identification and one or more of the segments sent, wherein the patient experience data includes an indication of patient interaction with one or more of the sent segments;

cause a processor to encrypt the patient identification;

cause a processor to record the patient experience data with the encrypted patient identification at the back end server;

receive, via the Internet, a request from a medical practice front end computing device at the back end server for at least a portion of the patient experience data, the request including the patient identification;

cause a processor to encrypt the patient identification from the request;

cause a processor to determine match the encrypted patient identification from the request to the encrypted patient identification that is stored with portion of the patient experience data to satisfy the request;

cause a processor to send, via the Internet, the determined matched portion of the patient experience data to the medical practice front end computing device in response to the request from the medical practice front end computing device;

wherein the request allows the medical practice to monitor the progress of the patient viewing the interactive multi-media segments.

* * * * *